(12) United States Patent
Anschel

(10) Patent No.: US 7,862,516 B1
(45) Date of Patent: Jan. 4, 2011

(54) ADHERENT VISUAL STIMULATOR

(76) Inventor: David Joseph Anschel, 1 Wildwood Rd., Rocky Point, NY (US) 11778

( * ) Notice: Subject to any disclaimer, the term of this patent is extended or adjusted under 35 U.S.C. 154(b) by 0 days.

(21) Appl. No.: 12/190,587

(22) Filed: Aug. 13, 2008

(51) Int. Cl.
*A61B 13/00* (2006.01)
(52) U.S. Cl. .................................................... 600/558
(58) Field of Classification Search ............... 600/26, 600/27, 544, 558; 607/1, 88, 91
See application file for complete search history.

(56) References Cited

U.S. PATENT DOCUMENTS 6,743,249 B1 * 6/2004 Alden ..................... 607/88

* cited by examiner

*Primary Examiner*—Max Hindenburg
*Assistant Examiner*—Jonathan M Foreman

(57) ABSTRACT

The present invention describes a novel device for the stimulation of the visual system for the purpose of recording evoked responses. The specific features of the device are particularly relevant to the elicitation of such responses in uncooperative subjects including the mentally impaired, young children, and those under the influence of anesthesia.

4 Claims, 2 Drawing Sheets

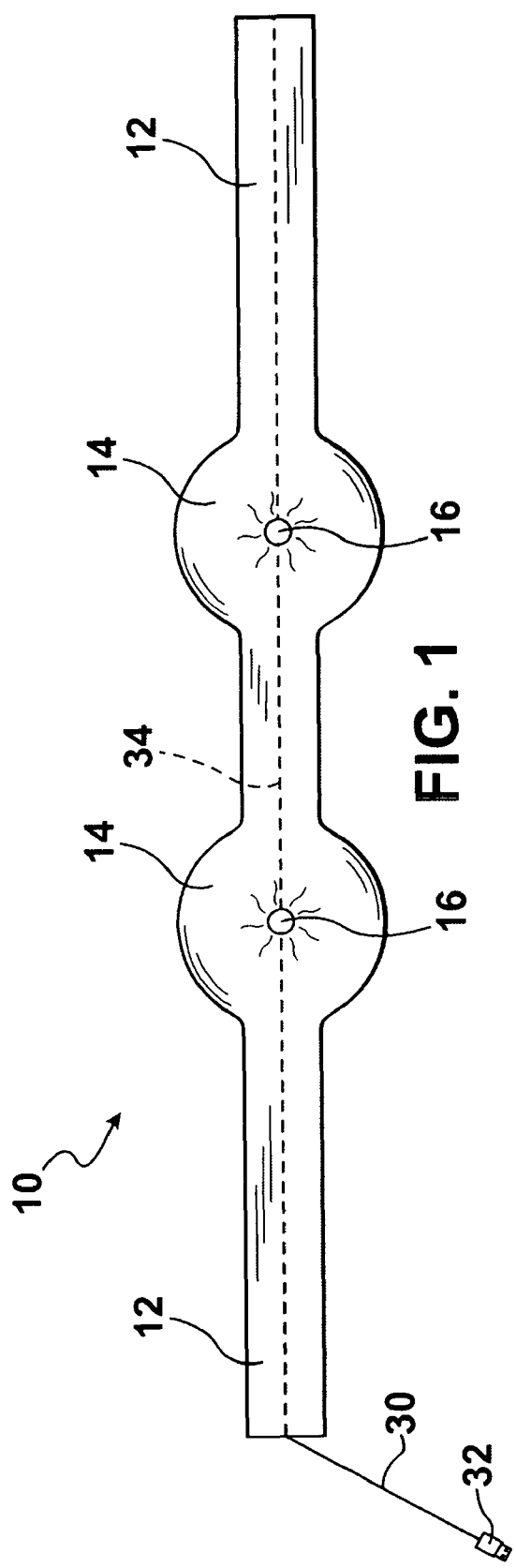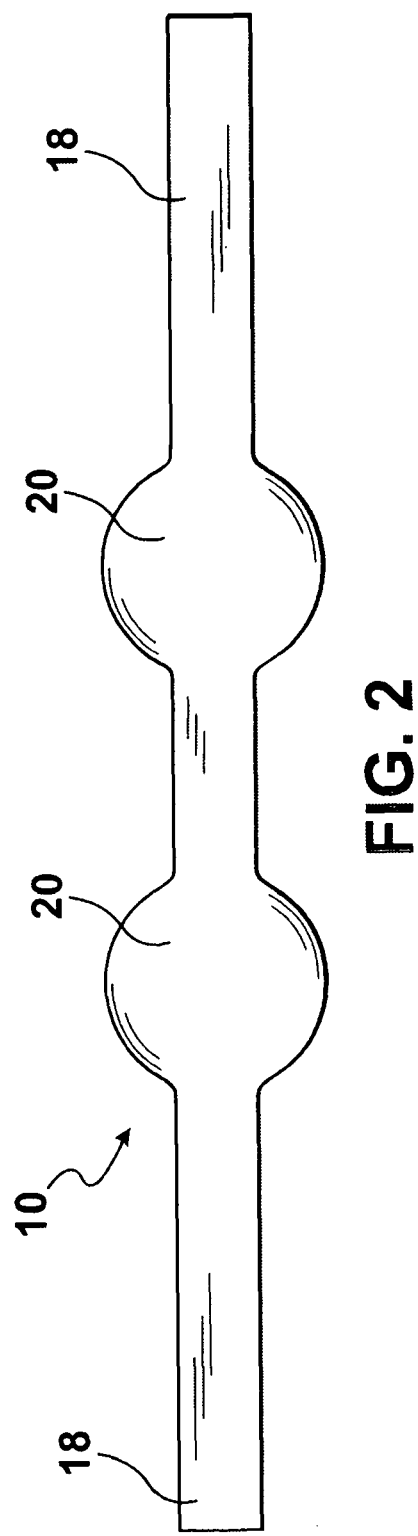

US 7,862,516 B1

ADHERENT VISUAL STIMULATOR

FIELD OF THE INVENTION

The present invention falls within the field of clinical neurophysiology. More specifically within devices for the assessment of the visual system through the presentation of stimuli to the eyes. The purpose of such stimulating devices is the generation of the electroretinogram, nerve action potentials, visual evoked potentials/responses and similar neurophysiological parameters.

BACKGROUND OF THE INVENTION

After entering the eyes, light passes through the lens and reaches the retina. Light will cause photoreceptor cells known as rods and cones to hyperpolarize. The photoreceptors synapse with other cells and eventually output is transmitted to the optic nerve.

The signal generated by the retina in response to a flash of light is known as the electroretinogram. This response may be recording using conventional neurophysiological equipment and reflects overall retinal function.

The optic nerves from each eye progress medially as they pass into the vault of the skull and shortly reach the optic chiasm. It is along the course of the optic nerves that nerve action potentials may be measured intraoperatively. At the optic chiasm fibers from the temporal portion (nasal visual field) of the retina continue on ipsilaterally into the optic tract, while the nasal portion (temporal visual field) crosses the midline and enters the contralateral optic tract. The optic tract fibers then enter alternating layers of the lateral geniculate nucleus. Axons then project toward the cortex, thus forming the optic radiations, and eventually reaching the occipital cortex. It is this visual cortex which is responsible for generating the major components of what is commonly referred to as a visual evoked potential (visual evoked response).

The majority of routine clinical evoked potential testing is performed upon awake, cooperative subjects using an alternating checkerboard pattern as the stimulus. In order to be an effective stimulus, the subject must keep his eyes open and focus on the changing pattern. In those subjects who cannot cooperate, the alternating checkerboard pattern is not useful. Common examples of such subjects include the mentally impaired, young children, and those under the influence of anesthesia. Frequently a flashing light is used in order to obtain a response in such individuals. Additionally a flash is the typical way of eliciting an electroretinogram in order to assess retinal function.

It has proven to be an exceptionally difficult task to employ such flash visual evoked responses in the operating room. A traditional strobe light is not feasible as it would be too distracting to the operating room staff and difficult to aim at the subject's eyes. Therefore reusable goggles with light emitting diodes have been employed. Unfortunately, the results obtained with such equipment has been sub-optimal. Problems include: 1.) A reusable device must be cleaned in between patients 2.) Tightly fitting goggles pose a risk of damaging the eyes 3.) Goggles may fall off the eyes or move intraoperatively and be difficult to reposition once the procedure is underway 4.) The light emitting diodes utilized, tend to be too weak to produce an adequate stimulus.

U.S. PATENT DOCUMENTS CITED

U.S. Pat. No. 4,618,230 to En et al. describes an entire visual stimulator system consisting of a stimulating bowl and specific recording apparatus. U.S. Pat. No. 4,676,611 to Nelson et al. describes a novel approach to presenting stimuli and analyzing the visual evoked potential.

OTHER REFERENCES

Studies of human visual pathophysiology with visual evoked potentials; Tobimatsu et al. Clinical Neurophysiology 117:1414-1433, 2006 Visual Evoked Potentials For Intraoperative Neurophysiologic Monitoring Using Total Intravenous Anesthesia; Wiedemayer et al. Journal of Neurosurgical Anesthesiology 15 (1): 19-24, 2003

SUMMARY OF THE INVENTION

The invention consists of light emitting diodes embedded within specifically shaped adhesive foam padding designed to conform to the periocular region of the human face. The purpose of the device is to stimulate the visual system for the recording of neurophysiological signals including the electroretinogram, optic nerve action potentials, and visual evoked potentials (visual evoked responses). This device will have several advantages over prior art, especially when employed in the operating room. These advantages include superior visual stimulation for the production of more reliable data, as well as improved safety and comfort for the subject.

BRIEF DESCRIPTION OF THE DRAWING

FIGS. 1 and 2 are pictorial representations of the stimulator in its embodiment with a single light emitting diode directed toward each eye (10).

FIG. 1 illustrates the portion which will be placed toward the subject's eyes. The major features are light emitting diodes (16), specially shaped adhesive foam padding which covers the eyes (14) and extends around the sides of the head (12), and a mechanism for interfacing with a triggering device. In this drawing the interface mechanism is a wire (30,34) which would carry a signal from a computer via USB connection (32) to the light emitting diodes.

FIG. 2 illustrates the aspect facing away from the subject and has a similar appearance, but the surface is non-adhesive and the light emitting diodes are covered by the opaque foam (20).

DETAILED DESCRIPTION OF THE INVENTION

Current methods of visual stimulation for the purpose of recording evoked responses (potentials) in uncooperative or anesthetized patients primarily rely upon the use of goggles with embedded light emitting diodes. These devices have shortcomings in that they are relatively unhygienic, fail to produce consistent responses in anesthetized patients, and pose a potential risk of damaging the eyes.

Figure 3:
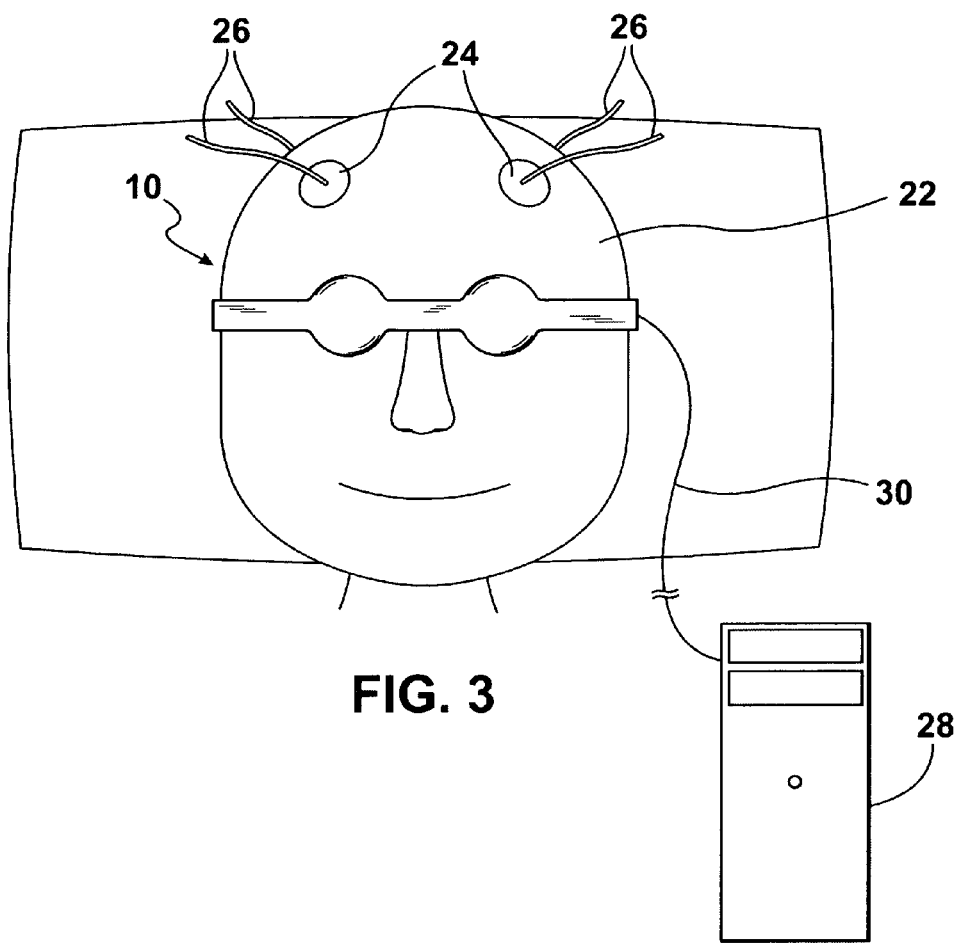
FIG. 3 depicts the invention in place on a subject (10). The stimulator is attached to the subject's head (22) and is connected via wire (30) to the triggering device (28). Recording electrodes (24) are shown with wires (26) which would be attached to the acquisition unit.
Figure 4:
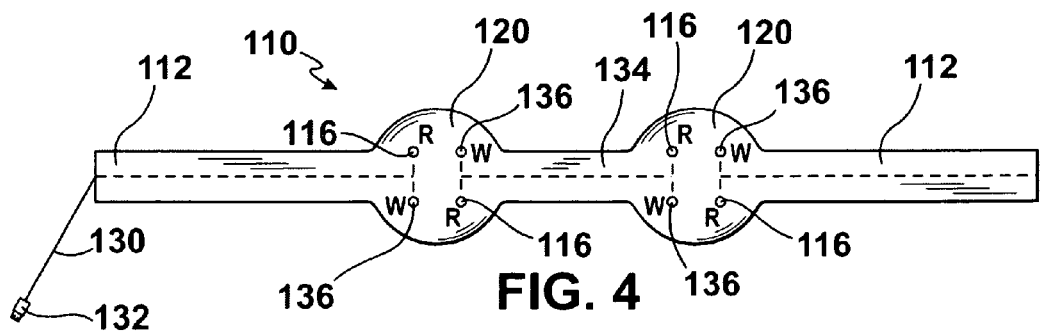
FIG. 4 illustrates an example of the invention with a 4 light emitting diode array containing interspersed red (116) and white (136) light emitting diodes. The other features are identical to those described for FIGS. 1 and 2.

The preferred embodiment of the invention is pictured in FIGS. 1, 2,3 and 4. It consists of the following key components:

1.) Adhesive foam padding shaped to the contours of the periocular region. The specific thickness and composition of the padding may be customized, but for most applications will be between 5-20 mm in thickness and composed of polyurethane or similar material. Additionally other methods of attachment may be employed such as Velcro, clasps, snaps etc.

2.) The light source consists of high intensity light emitting diodes or similar. By design, the present invention may be produced in different configurations. For example white or red light emitting diodes may be directed at each eye or different color/wavelength light sources may be interspersed.

3.) The light source will interface with a triggering device. At this point in time, this would most likely be via a USB wire connection. However any computer connection, including wireless methodology may be employed.

The present invention has several key advantages over prior art:

1.) The present invention will have hygienic advantages. Being disposable it will eliminate the necessity of cleaning and sterilization in between patients. Reusable stimulating goggles must be carefully cleaned and preferably sterilized after each use in the operating room. Additionally, some bodily fluids are extremely difficult to remove without damaging the reusable stimulating goggles. Using a disposable self adhesive visual stimulator will eliminate such problems.

2.) Ocular safety will be superior to prior art. Reusable stimulating goggles, may damage the eye, especially during procedures where the patient is placed face down. The disposable self adhesive visual stimulator consists primarily of foam padding and actually will add protection to the eyes rather than increasing the risk of damage caused by prior art.

3.) The form fitting and self-adhesive characteristics of the present invention will result in more effective acquisition of data. Prior art utilizes reusable stimulating goggles which are fastened to the patient's head with rubber straps. These straps often interfere with the surgical approach during intracranial procedures, thereby limiting their usefulness. Additionally, stimulating goggles may be accidentally moved from their original position during the operation, as the head is manipulated. It is often impossible to replace the goggles once the surgery has begun. A self adhesive visual stimulator will eliminate these problems, as there will not be a strap around the entire head and the adhesive properties of the present art will nearly eliminate any chance of the self adhesive visual stimulator moving as the head is manipulated.

4.) The specially designed high intensity light emitting diodes in close proximity to the eyes will provide a stronger stimulus than current goggles. Additionally, light sources of different wavelengths/colors may be employed in different arrangements in order to optimize responses.

While the present invention has been described and illustrated with respect to preferred embodiments, it is not intended to limit the invention, except as defined by the following claims. Furthermore, numerous modifications, changes, and improvements will occur to those skilled in the art without departing from the spirit and scope of the invention.

What is claimed is:

1. A method for assessing visual pathways comprising:
   providing a visual stimulator,
      wherein the visual stimulator comprises an adhesive opaque foam padding shaped to conform to the periocular region, at least one light emitting diode embedded within the padding, and a mechanism for interfacing with a triggering device;
   adhering the visual stimulator to a periocular region;
   stimulating the visual system by triggering the at least one light emitting diode with the triggering device;
   detecting and recording neurophysiolocigal signals in response to the stimulating of the visual system.

2. The method of claim 1, wherein the neurophysiological signals include one of an electroretinogram, optic nerve action potential, and visual evoked potential.

3. The method of claim 1, wherein the at least one light emitting diode includes a plurality of light emitting diodes having different colors.

4. The method of claim 1, wherein the at least one light emitting diode includes a plurality of light emitting diodes having different wavelengths.

* * * * *